(12) United States Patent
Knape et al.

(10) Patent No.: US 10,093,628 B2
(45) Date of Patent: Oct. 9, 2018

(54) COMPETITIVE PPAR-GAMMA ANTAGONISTS

(71) Applicant: FRAUNHOFER-GESELLSCHAFT ZUR FÖRDERUNG DER ANGEWANDTEN FORSCHUNG E.V., Munich (DE)

(72) Inventors: Tilo Knape, Berlin (DE); Andreas Von Knethen, Nidderau (DE); Michael John Parnham, Bad Soden am Taunus (DE); Manfred Schubert-Zsilavecz, Bad Homburg (DE); Mario Wurglics, Bad Homburg (DE); Daniel Flesch, Frankfurt am Main (DE)

(73) Assignee: FRAUNHOFER-GESELLSCHAFT ZUR FÖDERUNG DER ANGEWANDTEN FORSCHUNG E.V., Munich (DE)

( * ) Notice: Subject to any disclaimer, the term of this patent is extended or adjusted under 35 U.S.C. 154(b) by 0 days.

(21) Appl. No.: 15/500,330

(22) PCT Filed: Jul. 14, 2015

(86) PCT No.: PCT/EP2015/066085
§ 371 (c)(1),
(2) Date: Jan. 30, 2017

(87) PCT Pub. No.: WO2016/020156
PCT Pub. Date: Feb. 11, 2016

(65) Prior Publication Data
US 2017/0210711 A1   Jul. 27, 2017

(30) Foreign Application Priority Data

Aug. 4, 2014 (EP) ..................... 14179761
Oct. 7, 2014 (EP) ..................... 14187969

(51) Int. Cl.
*A61K 31/47* (2006.01)
*A61K 31/192* (2006.01)
*C07D 215/233* (2006.01)
*C07C 57/50* (2006.01)
*A61K 45/06* (2006.01)

(52) U.S. Cl.
CPC .......... *C07D 215/233* (2013.01); *A61K 31/47* (2013.01); *A61K 45/06* (2013.01)

(58) Field of Classification Search
CPC .. A61K 31/47; A61K 31/192; C07D 215/233; C07C 57/50
USPC ........................... 514/312; 546/153; 560/106
See application file for complete search history.

(56) References Cited

U.S. PATENT DOCUMENTS 7,005,440 B1  2/2006 Joyyosi et al.

FOREIGN PATENT DOCUMENTS

WO   WO-03043624 A1 *  5/2003  ........... A61K 31/155

OTHER PUBLICATIONS

Hieke et al. "SAR studies of acidic dual-secretase/PPAR modulators", Bioorganic & Medicinal Chemistry, Pergamon, GB, vol. 19, No. 18, Aug. 6, 2011 (Aug. 6, 2011), pp. 5372-5382, XP028389402.
Araújo et al. "PPAR gamma activation protects the brain against microvascular dysfunction in sepsis", Microvascular Research, vol. 84, No. 2, May 31, 2012, pp. 218-221.
Schmidt et al. "Peroxisome Proliferator-activated Receptor [gamma]-induced T Cell Apoptosis Reduces Survival during Polymicrobial Sepsis", American Journal of Repiratory and Critical Care Medicine, vol. 184, No. 1, Feb. 5, 2011, pp. 64-74.
Flesch et al. "SAR-studies of [gamma]-secretase modulators with PPAR [gamma]-agonistic and 5-lipoxygenase-inhibitory activity for Alzheimer's disease", Bioorganic & Medicinal Chemistry Letters, vol. 25, No. 4, Nov. 30, 2014, pp. 841-846.
International Search Report and Written Opinion, International Patent Application No. PCT/EP2015/066085, dated Oct. 14, 2015 (15 pages).

* cited by examiner

*Primary Examiner* — Matthew P Coughlin
*Assistant Examiner* — Sagar Patel
(74) *Attorney, Agent, or Firm* — Hamre, Schumann, Mueller & Larson, P.C.

(57) ABSTRACT

The present invention pertains to a new compound E)-2-(5-((4-methoxy-2-(trifluoromethyl)quinolin-6-yl)methoxy)-2-((4-(trifluoromethyl) benzyl)oxy)-benzylidene) hexanoic acid (MTTB), and its derivatives. The compounds of the invention are useful as selective peroxisome proliferator-activated receptor gamma (PPARγ) antagonists and are indicated for the use in the treatment of immune related diseases such as systemic inflammation, sepsis and septic shock.

15 Claims, 7 Drawing Sheets

COMPETITIVE PPAR-GAMMA ANTAGONISTS

FIELD OF THE INVENTION

The present invention pertains to a new compound E)-2-(5-((4-methoxy-2-(trifluoromethyl)quinolin-6-yl)methoxy)-2-((4-(trifluoromethyl) benzyl)oxy)-benzylidene) hexanoic acid (MTTB), and its derivatives. The compounds of the invention are useful as selective peroxisome proliferator-activated receptor gamma (PPARγ) antagonists and are indicated for the use in the treatment of immune related diseases such as systemic inflammation, sepsis and septic shock.

DESCRIPTION

Systemic inflammation, sepsis and septic shock are life threatening complications causing about 60000 deaths each year, therefore being the third most common cause of death in Germany. The incidence of this condition is rising due to the aging of the population and increasing numbers of immune-compromised and critically ill patients. Sepsis comprises a complex clinical syndrome that results from the body's response to infection caused by bacterial and/or fungal pathogens invading the body. Normally, a potent, complex, immunologic cascade ensures a prompt, protective response to microorganism invasion in humans. However, a deficient immunologic defense may allow infection to become established. Further, an excessive or poorly regulated response may harm the host through maladaptive release of endogenously generated inflammatory compounds. Sepsis is characterized by a hyper inflammatory phase followed by a hypo inflammatory phase, the latter also known as "immune paralysis". In particular the immune paralysis phase is critical for patients. Here T-cells of the adaptive immune system undergo apoptosis and stasis. Patients therefore often succumb to secondary infections.

Current approaches to treatment of sepsis focus on the hyper inflammatory phase of the disease in order to suppress disease progression. However, treatments are currently seldom successful as they dependent on a very early diagnosis of sepsis. Other therapeutic approaches merely target the symptoms of the disease. Known methods for treating sepsis include antibiotics, antibodies, small molecules and peptides, protein C, supportive therapy with oxygen, intravenous fluids, and medications that increase blood pressure.

However, despite the major advances of the past several decades in the treatment of serious infections, the incidence of sepsis and mortality due to sepsis continue to increase. There is, therefore, a need for new methods and compositions for the prevention and treatment of sepsis.

Peroxisome proliferator-activated receptor gamma (PPAR-γ or PPARG), expressed intracellularly in adipocytes, is a multifunctional nuclear receptor type transcription factor which plays a central role in the control of insulin sensitivity via the regulation of adipocyte gene expression and differentiation in response to prostanoid and thiazolidinedione (TZDs) ligands. It has also been identified as a key player in the modulation of cellular transdifferentiation, terminal differentiation of cancer cells and inflammatory processes. The protein is also expressed in other tissues such as colon and breast epithelial cells, bone marrow, leukocytic cell lines and T-cells, and, in macrophages, has been linked to the anti-inflammatory action of TZDs and their influence on the progression of atherosclerosis. Elevated expression of peroxisome proliferator-activated receptor gamma has been demonstrated in human primary and metastatic breast adenocarcinomas and in Alzheimer's disease brains while allelic variants have been reported in sporadic colon cancers.

As with other members of the nuclear hormone receptor superfamily, the tissue- and ligand-specific activation and transcriptional target gene regulation of PPARγ is a multi-step process (Kliewer et al., 1994, Seargent et al., 2004). This process involves specific binding of several natural and synthetic ligands (Forman et al., 1995, Kliewer et al., 1995), heterodimerisation with the retinoid X receptor alpha (RXRα), the recognition and interaction of sequence-specific PPARγ response elements (PPREs) in the promoter region of their target genes and finally the recruitment of cofactors and other nuclear coregulatory proteins (Nolte et al., 1998, Chawla et al., 2001, Kliewer et al., 2001, Spiegelman et al., 2004).

Because of its role during adipogenesis and in glucose metabolism, in which PPARγ predominantly induces gene expression of adipocyte protein 2 (aP2), cluster of differentiation 36 (CD36), lipoprotein lipase (LPL) or glucose transporter 4 (GLUT4), for example, it has been studied intensively as a therapeutic target (Lehmann et al., 1995, Tontonoz et al., 1995). The most prominent synthetic PPARγ agonists with high receptor affinity are the thiazolidinediones (TZDs). These are used in type-2 diabetes mellitus, in which they improve insulin sensitivity and cause a concomitant reduction of free glucose levels (Rangwala et al., 2004, Staels et al., 2005). PPARγ can also bind directly to other proteins and inhibits signal transduction. This capability, called transrepression, is mainly mediated by direct protein-protein interactions between PPARγ and other transcription factors, such as the nuclear factor "kappa-light-chain-enhancer" of activated B cells (NFkB), nuclear factor of activated T cells (NFAT) or the activator protein 1 (AP-1) (Yang et al., 2000, Wang et al., 2001, Chen et al., 2003).

In this way, PPARγ inhibits pro-inflammatory signaling and induces an anti-inflammatory response (Pascual et al., 2006, Ricote et al., 2007). In this context, activation of PPARγ by TZDs is effective in reducing inflammation. In contrast to the proven beneficial effects and widespread use of the TZDs in vivo, they are also associated with a number of deleterious side effects, serious tolerability and safety issues, including significant weight gain, peripheral oedema, congestive heart failure and bone fracture (Nesto et al., 2003, Nissen et al., 2007). On the other hand, PPARγ also induces apoptosis and thereby exerts immunosuppressive activity. Recently, PPARγ antagonism, especially by the PPARγ antagonist 2-chloro-5-nitrobenzanilide (GW9662) (Leesnitzer et al., 2002), has guided the development of new drugs and therapeutic strategies for a wide range of cancer types, such as breast cancer (Seargent et al., 2004, Burton et al., 2008), and modulation of immunity and inflammatory diseases (Schmidt et al., 2011). Because of the irreversible binding of GW9962 to the PPARγ protein, it is not suitable for therapeutic use. The increased understanding of the physiological role and clinical relevance of PPARγ has emphasized the critical need for the discovery, identification and characterisation of new PPARγ agonists, antagonists or selective PPARγ modulators (SPPARγMs), while avoiding the known side-effects.

Hence, until this day there is no satisfactory therapeutic approach for treating or preventing diseases characterized by a pathological inflammation such as sepsis and systemic inflammatory disorder. Furthermore, there is an ongoing need for the identification of selective PPAR antagonists with a more beneficial toxicological profile that could find application in the treatment of immune related or other diseases.

The above problem is solved in a first aspect by a compound of the formula (I), or a stereoisomer, derivative or salt thereof:

(I)

wherein $R_1$ and $R_2$ are independently selected from a non-substituted, monosubstituted or polysubstituted aryl or heteroaryl residue, and $R_1$ and $R_2$ are different, and $R_3$ is a non-substituted, monosubstituted or polysubstituted $C_1$-$C_{10}$-alkyl, wherein the alkyl can be straight, branched or cyclic.

In the context of the present invention the term "hetero aryl" encompasses monocyclic, bicyclic, or polycyclic hetero aromatic compounds having at least one hetero atom in the ring structure which may be nitrogen, oxygen or sulfur. Representative hetero aryl radicals falling within this definition are, for example, pyridine, quinoline, pyrrole, indole, thiophene, benzimidazole, tetrazole, pyrimidine and the like.

The term "aryl" denotes an aromatic radical, preferably of six to 10 carbon atoms, such as for example, phenyl, tolyl and the like. The term "hetero substituent" in the meaning of the present invention shall encompass any substituent having at least one non-carbon chain atom (hetero atom), preferably a hetero atom selected from oxygen, nitrogen or sulphur.

It was surprisingly discovered that the compounds of the present invention exhibited competitive antagonism when tested against PPAR gamma agonists, a very high cellular accumulation of the compounds of the invention, low cytotoxicity and minor PPAR gamma agonistic effects, compared to state of the art PPAR gamma antagonists such as GW9662.

Preferred embodiments of the invention pertain to compounds wherein $R_1$ and $R_2$ are monosubstituted or polysubstituted aryl or hetero aryl.

Another embodiment of the invention relates to compounds wherein $R_3$ is non-substituted $C_1$-$C_8$ alkyl, preferably non-substituted $C_2$-$C_6$ alkyl, most preferably non-substituted straight $C_4$ alkyl.

$R_1$ may in additional or alternative embodiments of the invention preferably be a radical with the formula (II), (II)

In formula (II) $R_4$ to $R_8$ are independently selected from H, OH, SH, a non-substituted, monosubstituted or polysubstituted $C_1$-$C_{18}$-alkyl, wherein the alkyl can be straight, branched or cyclic, alkenyl, trifluormethyl, a non-substituted, monosubstituted or polysubstituted aryl or heteroaryl residue, a non-substituted, monosubstituted or polysubstituted benzyl group, an acyl group, such as, for example, formyl, acetyl, trichloroacetyl, trifluoracetyl, fumaryl, maleyl, succinyl, benzoyl, or a branched or heteroatom- or aryl-substituted acyl group, an alkoxy substituent, such as, for example, —OMet, —OEt, —OnPr, -iPr, —OnBu, —OiBu, —OsecBu, —OtBu, the alkyl group thereof is branched, non-branched or cyclic, an alkyl group bound through a sulfur atom, such as, for example, —SMe, —SEt, or a sulfonyl group, such as, for example, —SO$_3$H, —SO$_2$Me, —SO$_2$CF$_3$, —SO$_2$C$_6$H$_4$CH$_3$ or SO$_2$C$_6$H$_4$CH$_2$Br, or a nitrogen substituent, such as, for example, —NH$_2$, —NHR, —NRR' (with R, R'=alkyl, aryl etc.), —NC or —NO2, or fluoro, chloro, bromo, iodo, —CN or a hetero substituent. More preferred is that $R_4$, $R_5$, $R_7$ and $R_8$ are H, and $R_6$ is trifluormethyl (—CF$_3$).

Additionally or alternatively the compound of the invention comprises $R_2$ which is a radical of the formula (III), (III)

wherein

X and Z are independently selected from C or N, $R_9$ to $R_{12}$ are independently selected from H, hydroxyl, a non-substituted, monosubstituted or polysubstituted $C_1$-$C_{18}$-alkyl, wherein the alkyl can be straight, branched or cyclic, alkenyl, trifluormethyl, a non-substituted, monosubstituted or polysubstituted aryl or heteroaryl residue, a non-substituted, monosubstituted or polysubstituted benzyl group, an acyl group, such as, for example, formyl, acetyl, trichloroacetyl, trifluoracetyl, fumaryl, maleyl, succinyl, benzoyl, or a branched or heteroatom- or aryl-substituted acyl group, an alkoxy substituent, such as, for example, —OMet, —OEt, —OnPr, -iPr, —OnBu, —OiBu, —OsecBu, —OtBu, the alkyl group thereof is branched, non-branched or cyclic, an alkyl group bound through a sulfur atom, such as, for example, —SMe, —SEt, or a sulfonyl group, such as, for example, —SO$_3$H, —SO$_2$Me, —SO$_2$CF$_3$, —SO$_2$C$_6$H$_4$CH$_3$ or SO$_2$C$_6$H$_4$CH$_2$Br, or a nitrogen substituent, such as, for example, —NH$_2$, —NHR, —NRR' (with R, R'=alkyl, aryl etc.), —NC or —NO2, or fluoro, chloro, bromo, iodo, —CN or a hetero substituent.

In this embodiment Z is preferably N, and X is preferably C.

Furthermore it may be preferred that $R_{10}$ and $R_{12}$ are H, $R_9$ is —OMet (—OCH$_3$), and $R_{11}$ is trifluormethyl (—CF$_3$).

Most preferred in context of the present invention is (E)-2-(5-((4-methoxy-2-(trifluoromethyl)quinolin-6-yl) methoxy)-2-((4-(trifluoromethyl) benzyl)oxy)-benzylidene) hexanoic acid (MTTB), having the formula (IV):

(IV)

Particularly preferred subgroups of compounds pertain to the following general structural formula with the afore described definitions of radicals $R_1$ to $R_{12}$.

Compounds having the general formula (V):

(V)

$R_2$ is selected from a non-substituted, monosubstituted or polysubstituted aryl or heteroaryl residue, preferably $R_2$ is a radical of the formula (III), (III)

wherein

X and Z are independently selected from C or N,

$R_9$ to $R_{12}$ are independently selected from H, hydroxyl, a non-substituted, monosubstituted or polysubstituted $C_1$-$C_{18}$-alkyl, wherein the alkyl can be straight, branched or cyclic, alkenyl, trifluormethyl, a non-substituted, monosubstituted or polysubstituted aryl or heteroaryl residue, a non-substituted, monosubstituted or polysubstituted benzyl group, an acyl group, such as, for example, formyl, acetyl, trichloroacetyl, trifluoracetyl, fumaryl, maleyl, succinyl, benzoyl, or a branched or heteroatom- or aryl-substituted acyl group, an alkoxy substituent, such as, for example, —OMet, —OEt, —OnPr, -iPr, —OnBu, —OiBu, —OsecBu, —OtBu, the alkyl group thereof is branched, non-branched or cyclic, an alkyl group bound through a sulfur atom, such as, for example, —SMe, —SEt, or a sulfonyl group, such as, for example, —SO$_3$H, —SO$_2$Me, —SO$_2$CF$_3$, —SO$_2$C$_6$H$_4$CH$_3$ or SO$_2$C$_6$H$_4$CH$_2$Br, or a nitrogen substituent, such as, for example, —NH$_2$, —NHR, —NRR' (with R, R'=alkyl, aryl etc.), —NC or —NO2, or fluoro, chloro, bromo, iodo, —CN or a hetero substituent.

In this embodiment Z is preferably N, and X is preferably C.

Furthermore it may be preferred that $R_{10}$ and $R_{12}$ are H, $R_9$ is —OMet (—OCH$_3$), and $R_{11}$ is trifluormethyl (—CF$_3$).

Alternatively or additionally $R_4$ to $R_8$ are independently selected from H, OH, SH, a non-substituted, monosubstituted or polysubstituted $C_1$-$C_{18}$-alkyl, wherein the alkyl can be straight, branched or cyclic, alkenyl, trifluormethyl, a non-substituted, monosubstituted or polysubstituted aryl or heteroaryl residue, a non-substituted, monosubstituted or polysubstituted benzyl group, an acyl group, such as, for example, formyl, acetyl, trichloroacetyl, trifluoracetyl, fumaryl, maleyl, succinyl, benzoyl, or a branched or heteroatom- or aryl-substituted acyl group, an alkoxy substituent, such as, for example, —OMet, —OEt, —OnPr, -iPr, —OnBu, —OiBu, —OsecBu, —OtBu, the alkyl group thereof is branched, non-branched or cyclic, an alkyl group bound through a sulfur atom, such as, for example, —SMe, —SEt, or a sulfonyl group, such as, for example, —SO$_3$H, —SO$_2$Me, —SO$_2$CF$_3$, —SO$_2$C$_6$H$_4$CH$_3$ or SO$_2$C$_6$H$_4$CH$_2$Br, or a nitrogen substituent, such as, for example, —NH$_2$, —NHR, —NRR' (with R, R'=alkyl, aryl etc.), —NC or —NO2, or fluoro, chloro, bromo, iodo, —CN or a hetero substituent. More preferred is that $R_4$, $R_5$, $R_7$ and $R_8$ are H, and $R_6$ is trifluormethyl (—CF$_3$).

Also preferred are compounds having the general formula (VI):

(VI)

$R_2$ is selected from a non-substituted, monosubstituted or polysubstituted aryl or heteroaryl residue, preferably $R_2$ is a radical of the formula (III), (III)

wherein
X and Z are independently selected from C or N,
$R_9$ to $R_{12}$ are independently selected from H, hydroxyl, a non-substituted, monosubstituted or polysubstituted $C_1$-$C_{18}$-alkyl, wherein the alkyl can be straight, branched or cyclic, alkenyl, trifluormethyl, a non-substituted, monosubstituted or polysubstituted aryl or heteroaryl residue, a non-substituted, monosubstituted or polysubstituted benzyl group, an acyl group, such as, for example, formyl, acetyl, trichloroacetyl, trifluoracetyl, fumaryl, maleyl, succinyl, benzoyl, or a branched or heteroatom- or aryl-substituted acyl group, an alkoxy substituent, such as, for example, —OMet, —OEt, —OnPr, -iPr, —OnBu, —OiBu, —OsecBu, —OtBu, the alkyl group thereof is branched, non-branched or cyclic, an alkyl group bound through a sulfur atom, such as, for example, —SMe, —SEt, or a sulfonyl group, such as, for example, —$SO_3H$, —$SO_2Me$, —$SO_2CF_3$, —$SO_2C_6H_4CH_3$ or $SO_2C_6H_4CH_2Br$, or a nitrogen substituent, such as, for example, —$NH_2$, —NHR, —NRR' (with R, R'=alkyl, aryl etc.), —NC or —$NO2$, or fluoro, chloro, bromo, iodo, —CN or a hetero substituent.

In this embodiment Z is preferably N, and X is preferably C.

Furthermore it may be preferred that $R_{10}$ and $R_{12}$ are H, $R_9$ is —OMet (—$OCH_3$), and $R_{11}$ is trifluormethyl (—$CF_3$).

For all compounds of formulas (V) and (VI) radicals corresponding to the above described $R_1$ and $R_2$ are different.

Another aspect of the present invention pertains to a method for producing or chemically synthesizing a compound of the present invention.

Preferably the method for producing or chemically synthesizing a compound of the present invention comprises the following steps:

(a)

(b)

(c)

(d)

wherein $R_1$ to $R_3$ are as defined above, and X is an reactive group, preferably Cl, Br, OTs, or OTf.

Yet another aspect then pertains to an antagonist of peroxisome proliferator-activated receptor gamma (PPARγ) for use in the treatment or prevention of immune diseases. In this aspect it may be preferred that the PPARγ antagonist is a selective PPARγ antagonist, therefore a PPARγ antagonist that does not, or only weakly (preferably under 50%, more preferably under 40%, 30%, 20% and most preferably under 10%) induces or transactivates PPARγ. Such selective compounds are in particular the compounds of the herein described new class of PPARγ antagonists.

In context of the present invention it was furthermore found that selective antagonists of PPARγ are useful in the treatment of immune diseases. The term "immune disease" or "immune-related diseases" for the purpose of the present invention shall be understood to refer to a disease or condition characterized by a pathological activation or repression of the immune system. In preferred embodiments the immune disease is systemic inflammation or sepsis. Most preferred the immune disease is sepsis in the hypo-inflammatory phase.

The antagonist of PPARγ for the herein described medical use is preferably a compound of the herein above and below described invention, most preferably the compound MTTB.

As used herein, the terms "treatment" and "treat" refer to both prophylactic or preventive treatment and curative or disease-modifying treatment, including treatment of patients at risk of contracting a disease or suspected to have contracted a disease, as well as patients who are ill or have been diagnosed as suffering from a disease or medical condition. The terms "treatment" and "treat" also refer to the maintenance and/or promotion of health in an individual not suffering from a disease but who may be susceptible to the development of an unhealthy condition, such as pathologically active or repressed immunity. Consequently, an "effective amount" is an amount that treats a disease or medical condition in an individual or, more generally, provides a nutritional, physiological, or medical benefit to the individual.

Preferably a treatment or prevention of immune diseases of the invention comprises the administration of a therapeutically effective dose of said antagonist of PPARγ to a subject suffering from, or at risk to develop an immune disease. The treatment or prevention of immune diseases may comprise the administration of additional therapeutically active compounds to said subject, wherein the additional therapeutically active compounds are effective and/or beneficial in the treatment of an immune disease, such as sepsis, systemic inflammation or septic shock.

The additional therapeutically active compounds of the present invention are preferably selected from another PPARγ antagonist, an immune suppressive agent, an antibiotic, a vasopressor, a corticosteroids, or activated protein C.

Therapeutically active or effective doses of the compounds of the invention will generally be in the range of 0.1 to 100 mg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. The compounds of the invention will commonly be administered over a period of up to 28 days. More commonly, the proteins will be administered over one week or less, often over a period of one to three days. In general, a therapeutically effective amount of the compounds of the invention is an amount sufficient to produce a clinically significant decrease of the hypo-inflammatory phase of sepsis.

Generally, the dosage of administered PPARγ antagonist of the invention will vary depending upon such factors as the patient's age, weight, height, sex, general medical condition and previous medi-cal history. Typically, it is desirable to provide the recipient with a dosage of PPARγ antagonist of the invention which is in the range of from about 1 pg/kg to 10 mg/kg (amount of agent/body weight of patient), although a lower or higher dosage also may be administered as circumstances dictate. Specific embodiments of the pharmaceutical compositions of the invention are provided herein below.

The object of the present invention is additionally solved by a combination comprising (a) an antagonist of PPARγ, and (b) a second compound that is effective in the treatment of sepsis or systemic inflammation.

The combination of the invention comprises preferably as agent (a) the antagonist of PPARγ as described herein above, most preferably MTTB or its derivatives. Agent (b), the second compound that is effective in the treatment of sepsis or systemic inflammation, is preferably selected from another PPARγ antagonist, an immune suppressive agent, an antibiotic, a vasopressor, a corticosteroids, or activated protein C.

The combination of the invention is for use in the treatment of immune diseases, as described herein above.

Furthermore provided is an in-vitro (ex-vivo) method for inhibiting PPARγ in a cell. The method comprises the step of contacting the cell with a compound as described herein before.

Diseases and Conditions

The present invention provides a new class of PPARγ antagonists which are useful as therapeutics in the treatment or prevention of immune related diseases or pathological apoptosis, such as diseases characterized by an excessive apoptosis of cells, for example chronic HIV, EBV or HCV infection, Alzheimer's disease, Parkinson's disease, or ischemic heart disease. In accordance with the present invention the compounds and compositions are particularly useful for the treatment and or prevention of a condition characterized by a pathological activated immune or inflammatory response. In particular the invention seeks to provide a treatment for sepsis, septic shock and systemic inflammatory disorder.

Compositions and Kits for Treating or Preventing Immune-Related Diseases

Another aspect of the present application relates to compositions, pharmaceutical compositions and kits for treating or preventing immune related diseases. In one embodiment, the composition comprises a compound, combination or composition as described herein, optionally together with a pharmaceutically acceptable carrier.

As used herein the language "pharmaceutically acceptable carrier" is intended to include any and all solvents, solubilizers, fillers, stabilizers, binders, absorbents, bases, buffering agents, lubricants, controlled release vehicles, nanoparticles, liposomes, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions. In certain embodiments, the pharmaceutically acceptable carrier comprises serum albumin.

The pharmaceutical composition of the invention is formulated to be compatible with its intended route of administration. Examples of routes of administration include parenteral, e.g., intrathecal, intra-arterial, intravenous, intradermal, subcutaneous, oral, transdermal (topical) and transmucosal administration.

Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injection use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a neuregulin) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, the pharmaceutical composition is formulated for sustained or controlled release of the active ingredient. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to viral antigens) or nanoparticles, including those prepared with poly(dl-lactide-co-glycolide), can also be used as pharmaceutically acceptable carriers. These can be prepared according to methods known to those skilled in the art.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. The pharmaceutical compositions can be included in a container, pack, or dispenser together with instructions for administration.

The present invention will now be further described in the following examples with reference to the accompanying figures and sequences, nevertheless, without being limited thereto. For the purposes of the present invention, all references as cited herein are incorporated by reference in their entireties. In the Figures:

FIG. 3: Comparison of the antagonistic effects of MTTB with those of GW9662 against increasing concentrations of rosiglitazone in vitro. To verify the agonistic and antagonistic effects of MTTB (A and C) and the reference PPARγ antagonist GW9662 (B and D) in HEK293T cells (A and B) and Jurkat T cells (C and D) a PPARγ-dependent transactivation assay was used. The cell lines were cultured with increasing doses (0.1 µM-10 µM) of rosiglitazone, MTTB or GW9662 alone or with the same concentrations of rosiglitazone in the presence of MTTB and GW9662 (1 µM or 10 µM) for 24 h. To determine the IC50 value for MTTB antagonism of response to rosiglitazone in HEK293T cells, a dose-response curve for MTTB antagonism was constructed using the PPARγ-dependent transactivation assay (E). Data show responses to 1 µM agonist (rosiglitazone) stimulation for 24 h in the presence of increasing concentrations of MTTB (0.1µ-50 µM). All values are means±SEM of four experiments. Each experiment in HEK293T cells was performed in quadruple and in Jurkat T cells in triplicate. Statistically significant differences from antagonist alone were obtained in response to rosiglitazone (1-10 µM) in the presence of MTTB at concentrations of x µM and y µM (p<0.05) in HEK293T cells and Jurkat T cells.

EXAMPLES

Materials and Methods
Chemicals and Reagents

All chemicals and reagents were of highest grade of purity and if not indicated otherwise, commercially available from AppliChem GmbH (Darmstadt, Germany), Carl Roth GmbH (Karlsruhe, Germany), Alfa Aesar GmbH (Karlsruhe, Germany), Apollo Scientific (Manchester, United Kingdom) and Sigma-Aldrich Chemie GmbH (Schnelldorf, Germany). The PPARγ antagonist GW9662, the SPPARγMs N-(9-fluorenylmethoxycarbonyl)-L-leucine (FMOC-L-leucine) and netoglitazone (MCC-555) were acquired from Cayman Chemical Company (Ann Arbor, USA) and the PPARγ agonist rosiglitazone from Enzo Life Sciences GmbH (Lörrach, Germany). Cell culture media and supplements were purchased from PAA Laboratories GmbH (Cölbe, Germany) and Sigma-Aldrich Chemie GmbH.

Cell Culture

Human T cell-78 (HuT-78) cells (Gazdar et al., 1980), Jurkat T cells (Schneider et al., 1977) and human embryonic kidney 293 cells, stably expressing the large T antigen of simian vacuolating virus 40 (HEK293T cells) (Graham et al., 1977) were obtained from LGC Standards GmbH (Wesel, Germany). HuT-78 cells and Jurkat T cells were cultured in Roswell Park Memorial Institute (RPMI) 1640 medium and HEK293T cells in Dulbecco's Modified Eagle's Medium (DMEM) in a humidified 5% carbon dioxide atmosphere at 37° C.

Both media contained 10% (v/v) heat-inactivated fetal calf serum, 100 units ml-1 penicillin and 100 µg ml-1 streptomycin. The media were changed three times a week and the cells passaged before reaching confluency. When using DMSO, in all cases, the final concentration of DMSO did not exceed 0.1% and was not found to be cytotoxic in the cell lines used.

Transient Transfection of Cultured Cells Lines

For the PPARγ-dependent transactivation assay, 1×104 HEK293T cells per well were seeded in 96-well plates and cultured overnight as described above to allow attachment of the HEK293T cells. The next day, the HEK293T cells were transiently transfected using the JetPRIME™ transfection reagent (PEQLAB Biotechnologie GmbH, Erlangen, Germany), as described by the manufacturer, with 0.01 µg per well pFA-PPARγ-LBD-GAL4-DBD, kindly provided by Prof. Dr. Manfred Schubert-Zsilavecz (Institute of Pharmaceutical Chemistry, Department of Biochemistry, Chemistry and Pharmacy, Goethe-University Frankfurt am Main, Germany), 0.09 µg per well pFR-Luc (Stratagene, La Jolla, USA) and 0.0005 µg per well pRL-CMV (Promega GmbH, Mannheim, Germany). After 4 h, the transfection medium was replaced and the HEK293T cells were cultured in fresh growth medium for another 24 h. For the transient transfection of 1×106 HuT-78 cells and Jurkat T cells per well, the SuperFect™ transfection reagent (QIAGEN GmbH, Hilden, Germany) was used as described by the producer with 0.2 µg per well pFA-PPARγ-LBD-GAL4-DBD, 0.8 µg per well pFR-Luc and 0.05 µg per well pRL-CMV. After 24 h, 1 ml fresh growth medium was added and the cells were cultured for another 48 h. The PPARγ-dependent transactivation assay in HEK293T cells using a 96-well plate format was performed in quadruple and in HuT-78 cells and Jurkat T cells using a 12-well plate format in triplicate.

PPARγ-Dependent Transactivation Assay of Cultured Cells Lines

The PPARγ-dependent transactivation assay is based on the vector pFA-PPARγ-LBD-GAL4-DBD encoding the hybrid protein PPARγ-LBD-GAL4-DBD and the reporter vector pFR-Luc, carrying a GAL4-responsive element in front of the Firefly luciferase gene. These two vectors were co-transfected, as described above, in combination with the control vector pRL-CMV, encoding *Renilla* luciferase, to normalize Firefly luciferase activity for transfection efficiency. Following transfection, the cells were incubated with MTTB, FMOC-L-leucine, MCC-555, GW9662 and rosiglitazone for varying times (2-48 h) and at increasing concentrations (0.01-10 µM), with or without rosiglitazone (0.01-10 µM). Transactivation was analysed using a 96-well plate format in a Mithras LB940 multimode reader (Berthold Technologies, Bad Wildbad, Germany). The IC50 value for MTTB was determined by fitting the data to a sigmoidal dose-response curve using the GraphPad Software Prism (La Jolla, USA).

Cell Viability Studies

HuT-78 cells, Jurkat T cells and HEK293T cells, were seeded in 96-well plates at a density of 5×104 cells per well and cultured overnight as described above to allow attachment of the HEK293T cells. The next day, the medium was replaced with fresh cell-specific growth medium containing varying concentrations of MTTB (1-30 µM) and GW9662 (1-30 µM). As control, DMSO alone was used. After 24 h stimulation, 3-(4, 5-dimethylthiazol-2-yl)-2, 5-diphenyltetrazolium bromide (MTT) solution (5 mg ml-1 in phosphate buffered saline (PBS)) was added and the cells were incubated for two more hours at 37° C. (Mosmann, 1983). Afterwards, the cells were lysed with MTT lysis buffer. Following cell lysis, cell viability was measured at an absorbance of 560 nm in a Mithras LB940 multimode reader. The cell viability studies using a 96-well plate format were performed in octet.

Determination of the Intracellular MTTB and GW9662 Accumulation

To determine the intracellular accumulation of MTTB and GW9662, HuT-78 cells, Jurkat T cells and HEK293T cells, were seeded in 12-well plates at a density of 5×104 cells per well and cultured overnight as described above to allow attachment of the HEK293T cells. The next day the medium was replaced with fresh cell-specific growth medium containing 10 µM MTTB and 10 µM GW9662. After 24 h treatment with MTTB and GW9662, the cells and the supernatant were harvested and analysed by LC-MS/MS. Accumulation was expressed as a percentage of the ratio of intracellular to extracellular concentration (I/E).

Computational Modeling

Computational docking was performed using the Molecular Operating Environment software suite 2012.10 (Chemical Computing Group Inc., Montreal, Canada). The assignment of hydrogens in the structure was performed using the Protonate3D routine (Labute, 2009).

Statistical Analysis

All data are presented as the means±standard error of the mean (SEM). Each experiment was performed at least three times. Statistical analysis was done either with one- or two-way-analysis of variance modified with Bonferroni's multiple comparison test or unpaired and paired Student's t-test, respectively. Differences were considered significant when: $p<0.05$.

Example 1: Synthesis of MTTB

The compounds of the invention, in particular MTTB are synthesized in a four stage process. In the following E refers to a reactant, P refers to a product of a reaction:

Stage 1:

In a three-neck reaction vessel with reflux condenser, argon supply, septum and magnet stirrer, E1 (1 eq) and $Cs_2CO_3$ (1.3 eq) are suspended in dimethylformamide (DMF) under inert gas and slightly heated (about 60° C. for about 15 min). After cooling to room temperature (RT), E2 (1 eq) is quickly added via a septum in few milliliters of

DMF and reacted under stirring without heating. After about 1.5 hours the solvent is removed under vacuum until nearly complete dryness. 50 ml of H₂O are added with 50 ml of ethyl acetate to separate phases. The hydrous phase is extracted three times with ethyl acetate, and the organic phase is dried over MgSO₄ and evaporated until complete dryness. The remainings underwent a column chromatography and after isolation the product was recrystallized two times (hexane/ethyl acetate).

Stage 2:

X = Cl, Br, OTs, OTf $R_1 = F_3C—Ph—$

In a three-neck reaction vessel with reflux condenser, argon supply, septum and magnet stirrer, P1 (1 eq) and Cs₂CO₃ (1.3 eq) are suspended in dimethylformamide (DMF) under inert gas and slightly heated (about 60° C. for about 15 min). After cooling to room temperature (RT), E3 (1 eq) is quickly added via a septum in few milliliters of DMF and reacted under stirring without heating. After about 1.5 hours the solvent is removed under vacuum until nearly complete dryness, 50 ml of H₂O are added with 50 ml of ethyl acetate to separate phases. The hydrous phase is extracted three times with ethyl acetate, and the organic phase is dried over MgSO₄ and evaporated until complete dryness. The remainings underwent a column chromatography and after isolation the product was recrystallized two times (hexane/ethyl acetate).

Stage 3:

In a three-neck reaction vessel with reflux condenser, argon supply, septum and magnet stirrer, NaH (1.3 eq) is first added under argon, and then suspended with tetrahydrofuran (THF). After about 15 min stirring and cooling E4 (1.3 eq) in THF is added drop-wise within few minutes. E4 can be prepared via Arbuzov reaction by refluxing the respective α-bromo-ester in triethylphosphite and distillation to yield E4. Then the mix is stirred for 30 to 60 minutes in an ice-bath. Via the septum the aldehyde (1 eq) in THF is added drop-wise. The reaction is observed via TLC. After completing the reaction (about 1 to 3 hours), the solvent is removed and the reaction is subject to a column chromatography. The purified product P3 is recrystallized (hexane/ethyl acetate).

Stage 4:

In a reaction vessel with reflux condenser and a heating bath, the ester in THF is combined with LiOH mono hydrate (10 eq) dissolved in H₂O. Methanol is added until the solution has only one phase and until complete hydrolysis heated at 40-60° C. while stirring. After about 12-72 hours THF and methanol are evaporated under vacuum. The acid is precipitated with 2N HCl. After removing the solvent from the precipitate and drying, the final product is obtained by recrystallization.

Example 2: MTTB Docks to the PPARγ-LBD

In a previous study it was shown that the similarity of the co-crystallized ligand is crucial for predictive modelling of the receptor-bound ligand conformation due to the pronounced induced fit known for PPARγ (Weber et al., 2012). Therefore, the inventors have chosen for comparison an X-ray structure of a potent sulfoncarboxamide antagonist in complex with the PPARγ-LBD (PDB code: 2HFP) (Hopkins et al., 2006).

Figure 1:
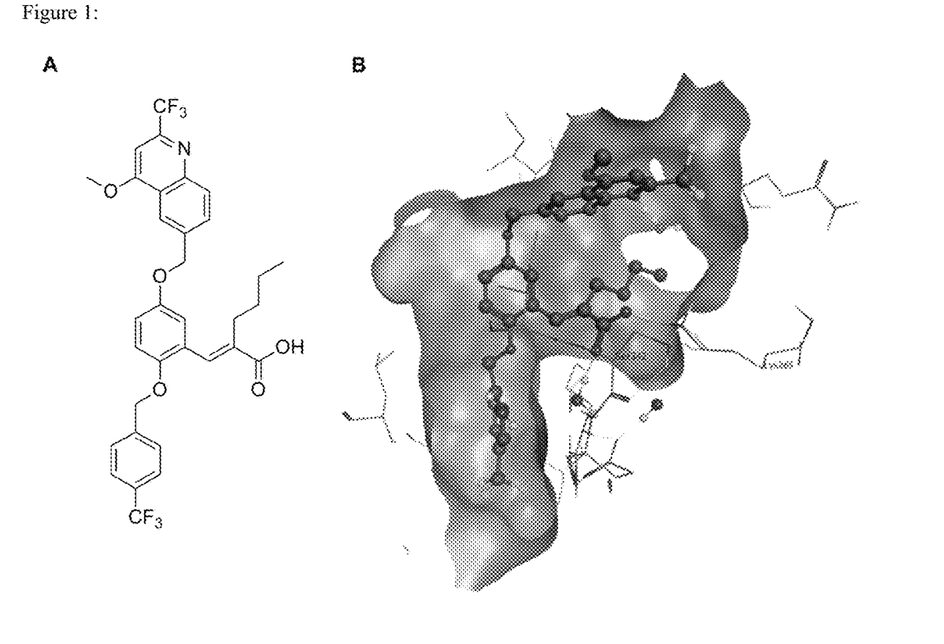
FIG. 1: Chemical structure and computational modelling of MTTB. The corresponding ligand incorporates all structural features of MTTB (A): an acidic head group, an adjacent lipophilic moiety and a central aromatic core with aromatic substituents on the opposite sites. The docking protocol converged yielding one single binding mode (B). The carboxylic moiety is engaged in ionic interactions with lysine 265 and hydrogen bond with the backbone amide of serine 323. The aromatic moieties and the alpha alkyl chain occupy the hydrophobic sites, indicating favourable interactions.

The corresponding ligand incorporates all the structural features of MTTB (FIG. 1A): an acidic head group, an adjacent lipophilic moiety and a central aromatic core with aromatic substituents on the opposite sites. The docking protocol converged, yielding one single binding mode as shown in FIG. 1B. The carboxylic moiety is engaged in ionic interactions with lysine 265 and a hydrogen bond with the backbone amide of serine 342. The aromatic moieties and the alpha alkyl chain occupy the hydrophobic sites, indicating favorable interactions. Pharmacophoric features situated on the moieties of the co-crystallized (vide supra) ligand were used for ligand placement. Water molecules remained in the binding site. The alpha HB score, which was shown to be well suited for docking in PPARγ-LBD (Weber et al., 2012), was used for initial scoring, GBVI/WSA dG, a forcefield based function, for refinement.

Example 3: MTTB Inhibits Rosiglitazone-Induced Transactivation of PPARγ

To analyse the agonistic and antagonistic effects of the PPARγ antagonist GW9662 (Leesnitzer et al., 2002), the SPPARγMs FMOC-L-leucine (Rocchi et al., 2001) and MCC-555 (Reginato et al., 1998) and the PPARγ agonist rosiglitazone (Willson et al., 1996) at the cellular level, a PPARγ-dependent transactivation assay was used in HEK293T cells. Firefly luciferase luminescence values and control Renilla luciferase luminescence values were determined in each sample. The ratios of Firefly to Renilla luciferase luminescence were used to normalize luciferase activity values.

Figure 2:
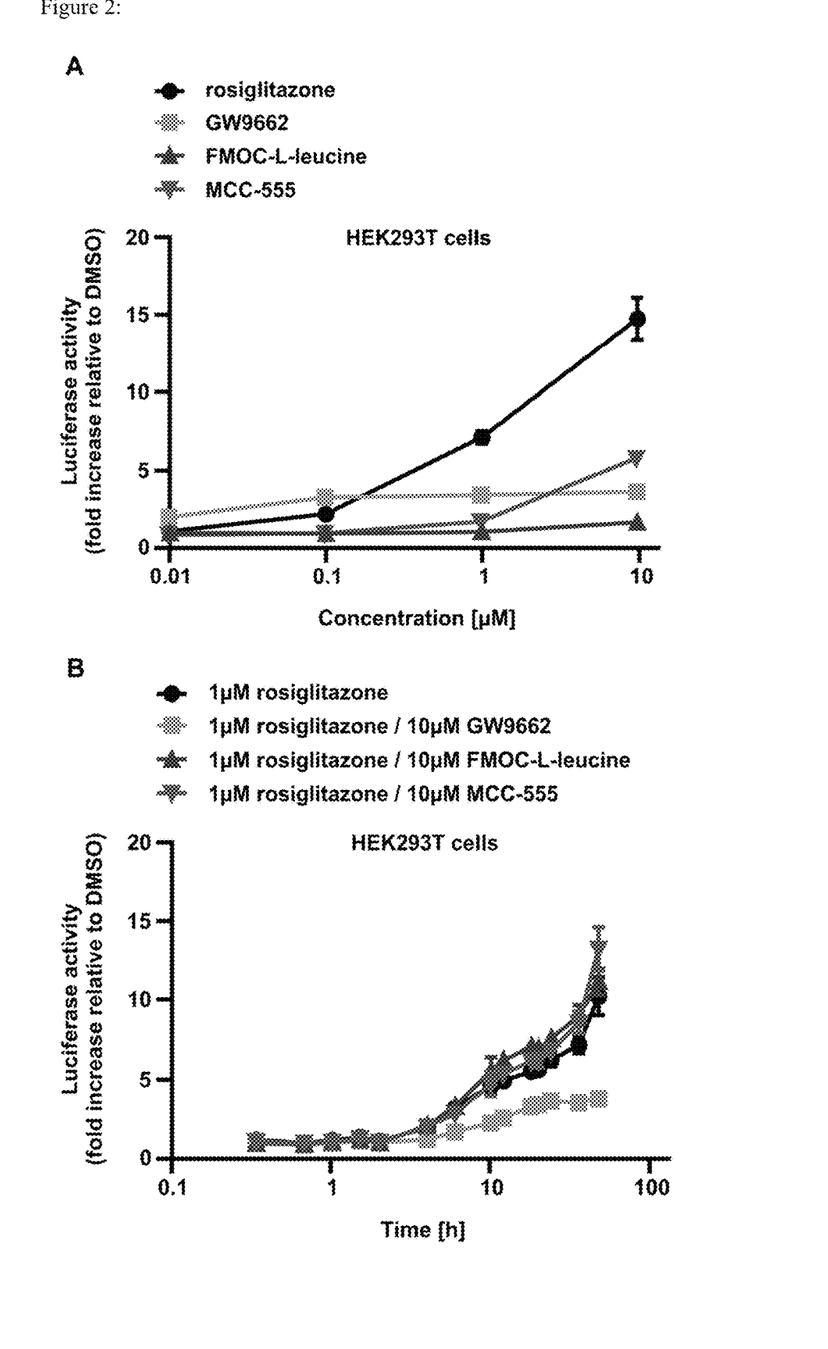
FIG. 2: Kinetic characterisation of a PPARγ agonist, a PPARγ antagonist and SPPARγMs in HEK293T cells. A PPARγ-dependent transactivation assay was used to verify the agonistic effects of the PPARγ agonist rosiglitazone, the antagonist GW9662 and the two SPPARγMs FMOC-L-leucine and MCC-555 after 24 h stimulation with different concentrations (0.01 µM-10 µM) of the compounds (A). To determine the antagonistic effects using 10 µM GW9662 and FMOC-L-leucine and MCC-555 in time course of the response to agonist (1 µM rosiglitazone) stimulation (B) the PPARγ-dependent transactivation assay was used again. Values are means±SEM of four experiments. Each experiment was performed in quadruple.

The agonist concentration curves to PPARγ receptor interacting agents exhibited differing courses after 24 h stimulation (FIG. 2A). Only rosiglitazone showed high agonistic effects and transactivated PPARγ in a dose-dependent manner. Surprisingly, GW9662 as an irreversible full PPARγ antagonist, showed agonistic effects and led to a dose-independent, 3-fold higher transactivation of PPARγ compared to DMSO control treatment. Higher concentrations (above 1 μM) of the SPPARγM MCC-555 transactivated PPARγ. In all cases, FMOC-L-leucine showed no agonistic effects. As shown in FIG. 2B, only the PPARγ antagonist GW9962 inhibited the time-course of the response to agonist (1 M rosiglitazone) stimulation. Neither SPPARγM, FMOC-L-leucine nor MCC-555, showed any antagonistic effects in the HEK293T cells. The very weak agonistic and non-existent antagonistic effects of FMOC-L-leucine and MCC-555 prompted us to use GW9662 for the following experiments and analyses as a reference compound.

Figure 3:
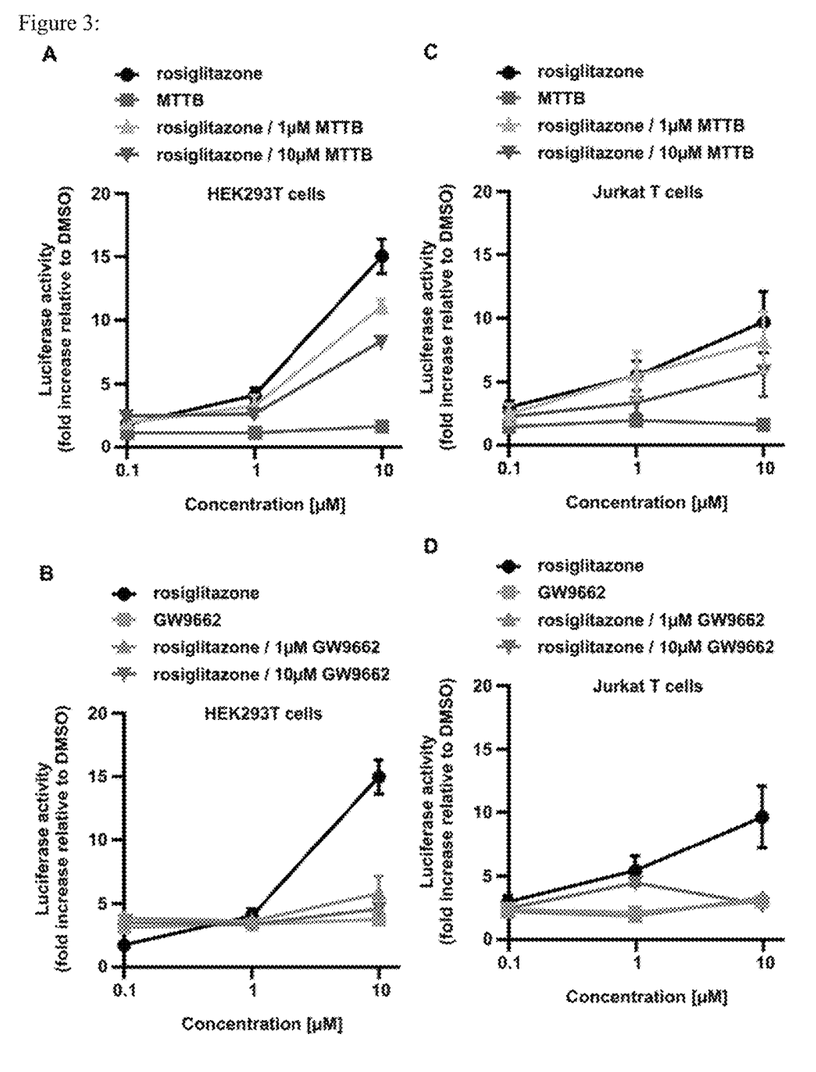

To verify the proposed interactions of MTTB with the PPARγ-LBD (FIG. 1B) and to test potential agonistic and antagonistic effects in HEK293T cells and Jurkat T cells, the compound was also tested in the PPARγ-dependent transactivation assay. The cells were cultured with different doses of MTTB and rosiglitazone alone or in combination for 24 h. As shown in FIGS. 3A and C, MTTB exhibited no agonistic effect in HEK293T cells and Jurkat T cells. In both cell lines, MTTB led to a dose-dependent inhibition of the rosiglitazone-induced transactivation of PPARγ with competitive antagonistic/partial agonistic characteristics. The reference compound GW9662 showed full antagonism and inhibited dose-independently the rosiglitazone-mediated PPARγ transactivation in HEK293T cells and Jurkat T cells (FIGS. 3B and D). However, GW9662 alone activated PPARγ and showed surprisingly high agonistic effects in the transactivation assay in both cell lines. As indicated in FIG. 3E, MTTB was able to inhibit the agonistic activity of rosiglitazone (1 μM) with an IC50 value of 4.3 μM after 24 h in HEK293T cells.

Example 4: Effects of MTTB and GW9662 on Cell Survival

Figure 4:
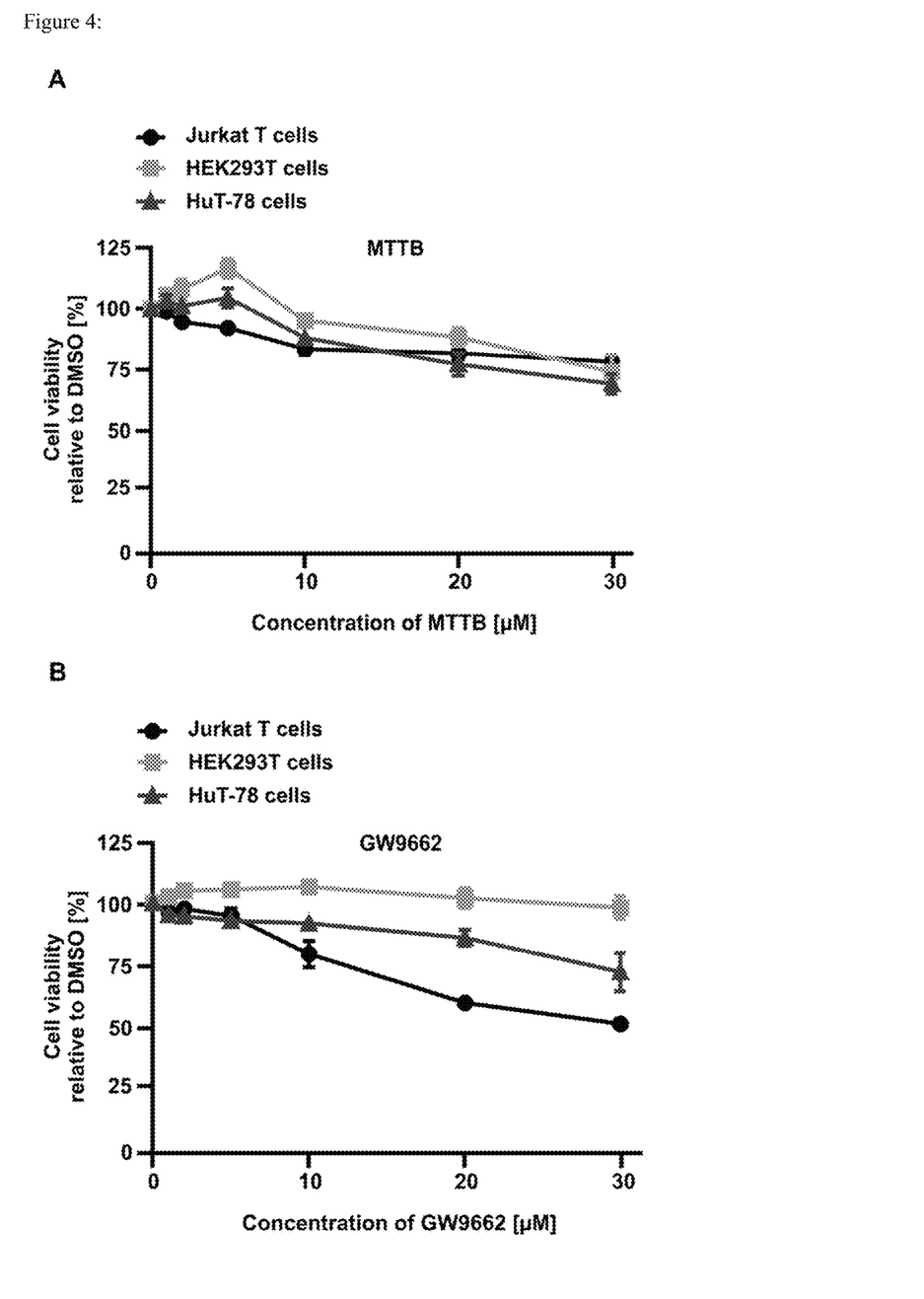
FIG. 4: Cytotoxicity of the competitive PPARγ antagonist MTTB and the PPARγ antagonist GW9662 in vitro. Cell viability of HEK293T cells, HuT-78 cells and Jurkat T cells was determined by MTT assay after 24 h stimulation with different concentrations (0.1 µM-30 µM) of MTTB (A) or the PPARγ antagonist GW9662 (B). The cell viability was calculated from the following equation: MTT optical density (OD) value of sample/MTT OD value of control (cells treated with DMSO). Data are shown as percent of solvent DMSO control and presented as means±SEM of three separate experiments. Each experiment was performed in octet.

To investigate the effects of MTTB and the reference compound GW9662 on survival of HEK293T cells, HuT-78 cells and Jurkat T cells, the cells were subjected to increasing doses (1-30 μM) of MTTB or GW9662 for 24 h. Cell viability was analysed by a MTT assay. MTTB was without cytotoxic effects at concentrations up to 10 μM (FIG. 4A). MTTB demonstrated comparable loss of viability in all three cell lines. In contrast, GW9662 showed varying cytotoxicity in the used cell lines (FIG. 4B). In HEK293T cells, up to a concentration of 30 μM, no loss of viability was detectable. In HuT-78 cells and Jurkat T cells, however, GW9662 was clearly cytotoxic at concentrations above 20 μM and 30 μM, respectively.

Example 5: MTTB Shows High Intracellular Accumulation

Figure 5:
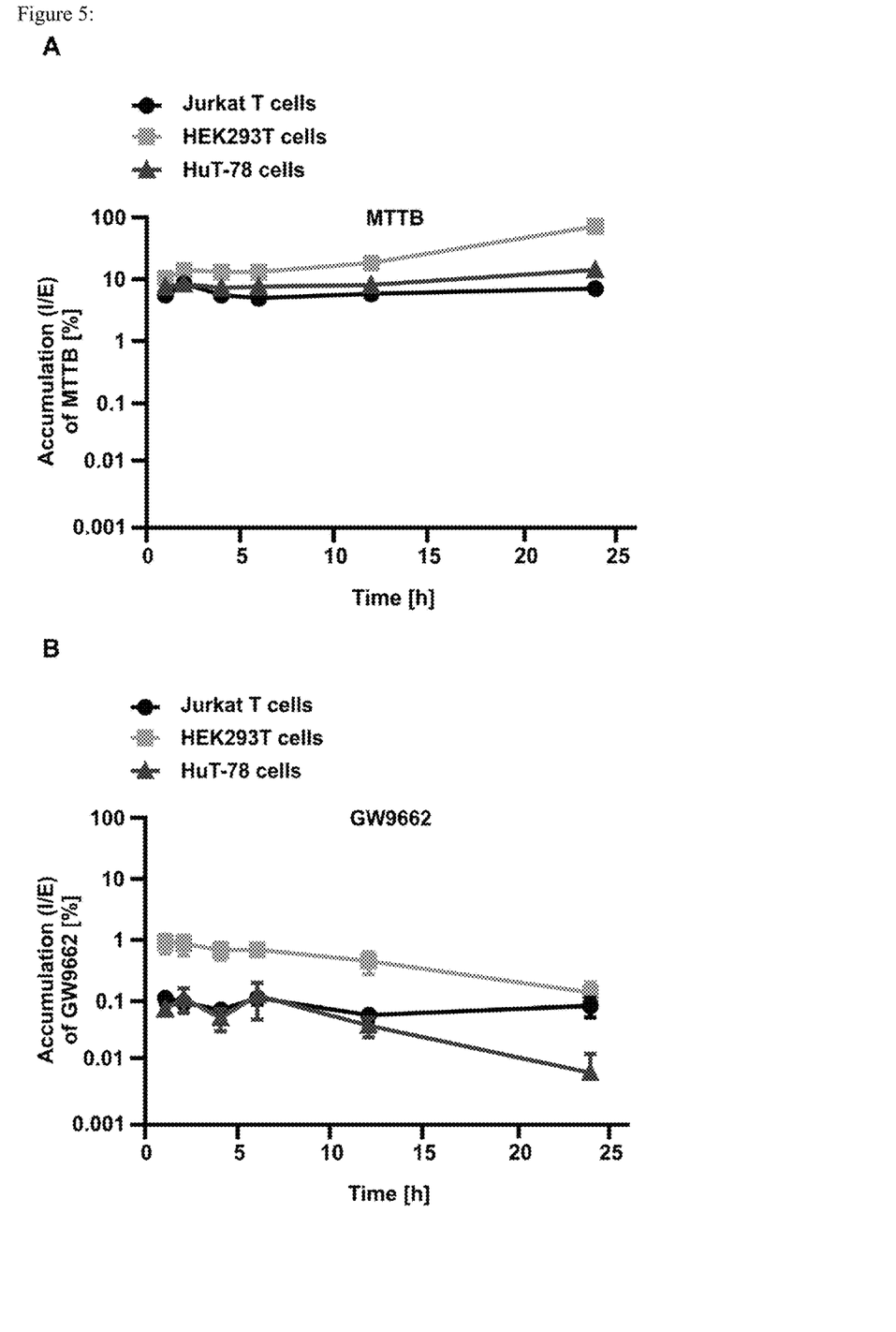
FIG. 5: Intracellular accumulation of MTTB and GW9662 in vitro. HEK293T cells, HuT-78 cells and Jurkat T cells were stimulated either with 10 µM MTTB (A) or 10 µM GW9662 (B) for 24 h. At different time-points the cells were harvested and the accumulation expressed as a percentage of the intracellular (I) to extracellular (E) concentration in µmol per $5 \times 10^5$ cells determined by LC-MS/MS. Values are means±SEM of three experiments.

The time-courses of the percentage intracellular accumulation of MTTB (10 μM) and the reference PPARγ antagonist GW9662 (10 μM) were analysed by LC-MS/MS. As shown in FIG. 5A, MTTB showed rapid sustained time-independent intracellular accumulation to approximately 10% after 24 h in HuT-78 cells and Jurkat T cells. In HEK293T cells, a time-dependent increase in the intracellular MTTB concentration was seen, achieving approximately 25% of the extracellular concentration after 24 h. As indicated in FIG. 5B, GW9662 showed 10-fold lower intracellular accumulation compared to MTTB decreasing with time in HEK293T cells. In HuT-78 cells and Jurkat T cells, the intracellular accumulation of GW9662 was about 100-fold less than that of MTTB (FIG. 5A). Especially in HuT-78 cells there was a rapid time-dependent decrease in the intracellular GW9662 accumulation.

Example 6: MTTB Significantly Enhances Survival in a Mouse Model of Sepsis

Figure 6:
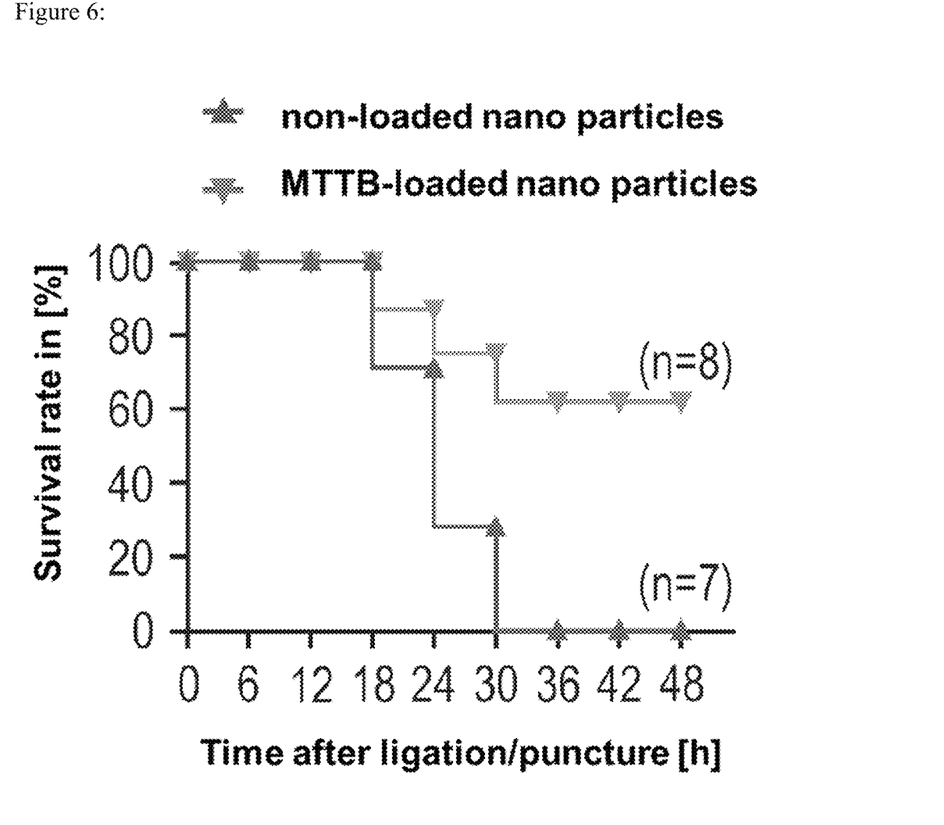
FIG. 6: Survival of Mice in a Sepsis Model after Treatment with MTTB.

The activity of MTTB was tested in a previously published mouse model of septic mice (Rittirsch D, Huber-Lang M S, Flierl M A, Ward P A. Immunodesign of experimental sepsis by cecal ligation and puncture. Nat Protoc 2009; 4: 31-36). In brief, the cecum ligation and puncture model (CLP) was performed as described by Rittirsch et al. using a 20-gauge puncture needle or without ligation and puncture for sham mice. MTTB loaded nano-particles were intraperitoneal applied 3 hours after ligation and puncturing. FIG. 6 shows a significant survival rate in-vivo of MTTB-treated septic mice compared to control nano-particles. This is a surprising demonstration of the applicability of the compounds of the invention in the treatment of immune diseases such as sepsis.

DISCUSSION AND CONCLUSIONS

The extensive clarification of PPARγ molecular interactions and signal transduction pathways, as well as its activation in molecular, cellular and clinical settings, has provided invaluable insights into the design of therapeutically useful PPARγ agonists and SPPARγMs (Willson et al., 2000, Sporn et al., 2001, Balint et al., 2006). While PPARγ activation by natural and synthetic ligands is well established (Forman et al., 1995, Kliewer et al., 1995), only little is known about PPARγ antagonism. However, increased understanding of the biological relevance of PPARγ antagonism emphasizes the critical need for the discovery of new therapeutically useful PPARγ antagonists, which do not exert known side-effects.

Currently, GW9662 is the best described and most prominent PPARγ antagonist (Leesnitzer et al., 2002), but it shows adverse properties including irreversible PPARγ antagonism. Therefore, the inventors have identified and characterised MTTB, from a screen of structurally related compounds, as a promising prototype for a new class of competitive PPARγ antagonists. Compared to the commercially available PPARγ antagonist GW9662, MTTB offers the possibility to regulate inhibition of PPARγ and immune responses and may be well suited for controlled therapeutic use in inflammatory conditions.

In line with Leesnitzer and colleagues, the inventors observed non-competitive irreversible antagonism with GW9662 (Leesnitzer et al., 2002) so that the rosiglitazone-mediated PPARγ transactivation was completely inhibited. Co-treatment of HEK293T cells and Jurkat T cells with rosiglitazone and GW9662 revealed the expected antagonistic effects. Interestingly, GW9662 alone led to dose-independent, approximately 3-fold PPARγ transactivation, which to the inventor's knowledge has not been reported before. These results suggest that GW9662 is not a classical full PPARγ antagonist in both HEK293T cells and Jurkat T cells, but rather acts as a SPPARγM (Olefsky et al., 2000, Knouff et al., 2004) with strong antagonistic and distinct dose-independent agonistic activity. Because of the irreversible binding and the dose-independent agonistic effects of GW9962 at the PPARγ protein, it is not suitable for therapeutic use.

GW9662 has been reported to act as a potent PPARγ antagonist with high-affinity and selectivity in both cell-free and cell-based assays (IC50 of 3.3 nM) and in human mammary tumour cell lines by covalently modifying the cysteine 285 residue in the ligand-binding site of PPARγ (Leesnitzer et al., 2002, Seargent et al., 2004). As a consequence, GW9662 fully and irreversibly abrogates PPARγ activation and signalling. The inventors observed only moderate or weak effects of the SPPARγMs, FMOC-L-leucine and MCC-555, while GW9662 and MTTB potently inhibited the action of rosiglitazone in both HEK293T cells and Jurkat T cells. With an IC50 of 4.3 µM in HEK293T cells, MTTB exhibited moderate dose-dependent, competitive antagonistic activity at lower concentrations than those reported for antagonism of PPARγ by GW9662 in cell lines. This competitive antagonistic potency of MTTB against rosiglitazone mediated PPARγ transactivation, was also verified in Jurkat T cells. In contrast to GW9662, MTTB showed less cytotoxicity in both HuT-78 cells and Jurkat T cells, indicating that at the concentrations tested, it is likely to exert pharmacological rather than toxicological effects on inflammatory cells. The inventor's observation of approximately 100-fold higher intracellular accumulation of MTTB, as compared to GW9662, into HuT-78 cells and Jurkat T cells, in contrast to HEK293T cells, in which uptake of MTTB was only 10-fold higher than of GW9662, suggests potential selectivity for lymphocytes.

Interestingly, structural and computational docking analysis of MTTB emphasizes the potential affinity of MTTB for the PPARγ-LBD and accentuates differences in the binding characteristics between MTTB, the antagonist GW9662 and the agonist rosiglitazone at PPARγ (Chandra et al., 2008).

Therefore MTTB will be used as a lead compound to enhance PPARγ binding affinity by modification of its external residues. Taking into consideration that subtle changes in ligand receptor interaction lead to differences in pharmacology as has already been shown for the structurally similar PPARγ TZD full agonists rosiglitazone and pioglitazone (Berger et al., 2005, Nissen et al., 2007), structural modifications may further improve the antagonistic effect of MTTB.

Because of the strong antagonistic activity of GW9662, it is widely used as a research tool in cell culture systems and animal models to study the role of PPARγ in biological processes. In contrast to the irreversible nature of GW9662 binding, MTTB appears to bindreversibly to the PPARγ protein. Taken together, the competitive antagonism, low partial agonism, low cytotoxicity and high intracellular uptake are properties which would allow safe and repeated dosing of MTTB for potential therapeutical use. Further studies in animal models are planned. The results presented here with MTTB indicate that it is a prototype of a new class of competitive PPARγ antagonists, and a promising candidate for a broadly applicable therapeutic approach to controlled treatment of inflammatory and immunological disorders.

The invention claimed is:

1. A compound of the formula (I), or a stereoisomer, or salt thereof:

(I)

wherein
R$_1$ is selected from a non-substituted, monosubstituted or polysubstituted aryl or heteroaryl residue,
R$_2$ is a radical of the formula (III), (III)

wherein

X and Z are independently selected from C or N,

$R_9$ to $R_{12}$ are independently selected from H, hydroxyl, a non-substituted, monosubstituted or polysubstituted $C_1$-$C_{18}$-alkyl, wherein the alkyl can be straight, branched or cyclic, alkenyl, trifluormethyl, a non-substituted, monosubstituted or polysubstituted aryl or heteroaryl residue, a non-substituted, monosubstituted or polysubstituted benzyl group, an acyl group, or a branched or heteroatom- or aryl-substituted acyl group, an alkoxy substituent, the alkyl group thereof is branched, non-branched or cyclic, an alkyl group bound through a sulfur atom, or a sulfonyl group, or a nitrogen substituent, or fluoro, chloro, bromo, iodo, —CN or a hetero substituent, if X is N then $R_{11}$ is absent, and if Z is N then $R_{12}$ is absent; and $R_1$ and $R_2$ are different, and $R_3$ is a non-substituted, monosubstituted or polysubstituted $C_1$-$C_{10}$-alkyl, wherein the alkyl can be straight, branched or cyclic.

2. The compound according to claim 1, wherein $R_3$ is non-substituted $C_1$-$C_8$ alkyl.

3. The compound according to claim 1, wherein $R_1$ is a radical with the formula (II), (II)

wherein $R_4$ to $R_8$ are independently selected from H, OH, SH, a non-substituted, monosubstituted or polysubstituted $C_1$-$C_{18}$-alkyl, wherein the alkyl can be straight, branched or cyclic, alkenyl, trifluormethyl, a non-substituted, monosubstituted or polysubstituted aryl or heteroaryl residue, a non-substituted, monosubstituted or polysubstituted benzyl group, an acyl group, or a branched or heteroatom- or aryl-substituted acyl group, an alkoxy substituent, the alkyl group thereof is branched, non-branched or cyclic, an alkyl group bound through a sulfur atom, or a sulfonyl group, or a nitrogen substituent, or fluoro, chloro, bromo, iodo, —CN or a hetero substituent.

4. The compound according to claim 3, wherein $R_4$, $R_5$, $R_7$ and $R_8$ are H, and $R_6$ is trifluormethyl (—$CF_3$).

5. The compound according to claim 1, wherein Z is N, and X is C.

6. The compound according to claim 5, wherein $R_{10}$ is H, $R_{12}$ is absent, $R_9$ is —OMet (—$OCH_3$), and $R_{11}$ is trifluormethyl (—$CF_3$).

7. A method for treating an immune disease in a subject in need thereof, the method comprising the step of administering to the subject a therapeutically effective amount of a compound according to claim 1.

8. A combination comprising (a) a compound according to claim 1, and (b) a second compound that is effective in the treatment of sepsis or systemic inflammation.

9. The combination according to claim 8, wherein the second compound (b) that is effective in the treatment of sepsis or systemic inflammation is selected from another PPARγ antagonist, an immune suppressive agent, an antibiotic, a vasopressor, a corticosteroids, or activated protein C.

10. A method for treating an immune disease in a subject in need thereof, the method comprising the step of administering to the subject a therapeutically effective amount of the combination according to claim 8.

11. A pharmaceutical composition, comprising a compound according to claim 1, or a combination according to claim 10, together with a pharmaceutically acceptable carrier, adjuvant, diluent and/or excipient.

12. The method according to claim 7, wherein the immune disease is systemic inflammation or sepsis.

13. The compound according to claim 1, wherein $R_3$ is non-substituted $C_2$-$C_6$ alkyl.

14. The compound according to claim 1, wherein $R_3$ is non-substituted straight $C_4$ alkyl.

15. The compound according to claim 6, wherein the compound is (E)-2-(5-((4-methoxy-2-(trifluoromethyl)quinolin-6-yl)methoxy)-2-((4-(trifluoromethyl) benzyl)oxy)-benzylidene) hexanoic acid (MTTB).

* * * * *